(12) United States Patent
Schuchardt et al.

(10) Patent No.: US 12,370,034 B2
(45) Date of Patent: Jul. 29, 2025

(54) Y-SHAPED SACROCOLPOPEXY SUPPORT

(71) Applicant: Coloplast A/S, Humlebaek (DK)

(72) Inventors: Sarah J. Schuchardt, Minneapolis, MN (US); Michael M. Witzmann, Shoreview, MN (US); John J. Allen, Mendota Heights, MN (US); David Richmond, Prestwick (GB); Matthew George Litton, Prestwick (GB)

(73) Assignee: Coloplast A/S, Humlebaek (DK)

( * ) Notice: Subject to any disclaimer, the term of this patent is extended or adjusted under 35 U.S.C. 154(b) by 350 days.

(21) Appl. No.: 17/979,287

(22) Filed: Nov. 2, 2022

(65) Prior Publication Data

US 2023/0118607 A1 Apr. 20, 2023

Related U.S. Application Data

(63) Continuation of application No. 16/537,642, filed on Aug. 12, 2019, now Pat. No. 11,517,413, which is a (Continued)

(51) Int. Cl.
*A61F 2/00* (2006.01)
(52) U.S. Cl.
CPC .......... *A61F 2/0045* (2013.01); *A61F 2/0063* (2013.01); *A61F 2220/0025* (2013.01); (Continued)
(58) Field of Classification Search
CPC ................. A61F 2/0045; A61F 2/0063; A61F 2220/0025; A61F 2220/0075; (Continued)

(56) References Cited

U.S. PATENT DOCUMENTS 5,676,679 A 10/1997 Simon et al.
5,840,011 A 11/1998 Landgrebe et al.
(Continued)

FOREIGN PATENT DOCUMENTS

AU 2002241673 B2 8/2002
DE 19544162 C1 4/1997
(Continued)

OTHER PUBLICATIONS

Bard Nordic, Ajust TM Adjustable Single-Incision Sling, URL "http:/www.bardnordic.com/main/product.asp?sectionTypeid=2 &sectionid=6&productid=296" accessed Mar. 2, 2009.

*Primary Examiner* — Carrie R Dorna
*Assistant Examiner* — Joshua Daryl D Lannu
(74) *Attorney, Agent, or Firm* — Coloplast Corp., Coloplast A/S; Nick Baumann

(57) ABSTRACT

A Y-shaped support has a head section having a first free end and a second end secured to a leg section, with the leg section having a first leg extending from the second end of the head section and a second leg extending from the second end of the head section. A first connector is provided as a first interlocking stitch, with the first interlocking stitch passed through open leg spaces of the first leg and open head spaces in the head section. A second connector is provided as a second interlocking stitch, with the second interlocking stitch passed through the aligned open leg spaces of the first leg and the second leg to connect the first leg to the second leg. The second end of the head section is located outside a space where the first leg is connected to the second leg.

12 Claims, 11 Drawing Sheets

Related U.S. Application Data continuation of application No. 15/465,614, filed on Mar. 22, 2017, now Pat. No. 10,426,586.

(60) Provisional application No. 62/446,531, filed on Jan. 16, 2017.

(52) U.S. Cl.
CPC ............... *A61F 2220/0075* (2013.01); *A61F 2220/0091* (2013.01); *A61F 2230/006* (2013.01); *A61F 2250/0014* (2013.01); *A61F 2250/0015* (2013.01)

(58) Field of Classification Search
CPC ........ A61F 2220/0091; A61F 2230/006; A61F 2250/0014; A61F 2250/0015
See application file for complete search history.

(56) References Cited

U.S. PATENT DOCUMENTS

| | | |
|---|---|---|
| 6,221,005 B1 | 4/2001 | Bruckner et al. |
| 6,406,420 B1 | 6/2002 | McCarthy et al. |
| 6,527,794 B1 | 3/2003 | McDevitt et al. |
| 6,592,515 B2 | 7/2003 | Thierfelder et al. |
| 6,660,023 B2 | 12/2003 | McDevitt et al. |
| 6,695,855 B1 | 2/2004 | Gaston |
| 7,083,568 B2 | 8/2006 | Neisz et al. |
| 7,175,591 B2 | 2/2007 | Kaladelfos |
| 7,837,710 B2 | 11/2010 | Lombardo et al. |
| 7,901,346 B2 | 3/2011 | Kovac et al. |
| 7,985,173 B2 | 7/2011 | Jacquetin |
| 8,585,578 B2 | 11/2013 | Morningstar et al. |
| 8,585,579 B2 | 11/2013 | Moschel et al. |
| 8,608,643 B2 | 12/2013 | Morningstar et al. |
| 8,696,544 B2 | 4/2014 | Deegan et al. |
| 8,720,446 B2 | 5/2014 | Deitch |
| 2002/0028980 A1* | 3/2002 | Thierfelder ...... A61B 17/00234 600/30 |
| 2002/0072694 A1 | 6/2002 | Snitkin et al. |
| 2002/0103542 A1 | 8/2002 | Bilbo |
| 2003/0130670 A1 | 7/2003 | Anderson et al. |
| 2003/0181946 A1 | 9/2003 | Bartlett |
| 2003/0199729 A1 | 10/2003 | Grise |
| 2003/0220538 A1 | 11/2003 | Jacquetin |
| 2003/0229361 A1 | 12/2003 | Jackson |
| 2004/0039453 A1 | 2/2004 | Anderson et al. |
| 2004/0138706 A1 | 7/2004 | Abrams et al. |
| 2005/0004576 A1 | 1/2005 | Benderev |
| 2005/0021086 A1 | 1/2005 | De Leval |
| 2005/0055052 A1 | 3/2005 | Lombardo et al. |
| 2005/0075660 A1 | 4/2005 | Chu et al. |
| 2005/0277985 A1 | 12/2005 | Wert et al. |
| 2005/0288692 A1 | 12/2005 | Beraud et al. |
| 2006/0063968 A1 | 3/2006 | Anderson et al. |
| 2006/0089525 A1 | 4/2006 | Mamo et al. |
| 2006/0122457 A1 | 6/2006 | Kovac et al. |
| 2006/0205995 A1 | 9/2006 | Browning |
| 2006/0229596 A1 | 10/2006 | Weiser et al. |
| 2007/0021649 A1 | 1/2007 | Nowlin et al. |
| 2007/0038017 A1 | 2/2007 | Chu |
| 2007/0225546 A1 | 9/2007 | Anderson et al. |
| 2007/0293717 A1 | 12/2007 | Kaleta et al. |
| 2008/0021265 A1 | 1/2008 | Garbin et al. |
| 2008/0051836 A1 | 2/2008 | Foerster et al. |
| 2008/0139877 A1 | 6/2008 | Chu et al. |
| 2008/0140218 A1 | 6/2008 | Staskin et al. |
| 2008/0196729 A1 | 8/2008 | Browning |
| 2008/0287956 A1 | 11/2008 | Smith et al. |
| 2008/0287968 A1 | 11/2008 | Smith et al. |
| 2009/0137862 A1 | 5/2009 | Evans et al. |
| 2009/0187067 A1 | 7/2009 | Carteron et al. |
| 2010/0030016 A1 | 2/2010 | Knoll |
| 2010/0063542 A1 | 3/2010 | van der Burg et al. |
| 2010/0121349 A1 | 5/2010 | Meier et al. |
| 2010/0198003 A1 | 8/2010 | Morningstar et al. |
| 2010/0198004 A1 | 8/2010 | Moschel et al. |
| 2010/0256442 A1 | 10/2010 | Ogdahl et al. |
| 2010/0305394 A1 | 12/2010 | Rosenblatt |
| 2011/0160527 A1 | 6/2011 | Khamis et al. |
| 2011/0263930 A1 | 10/2011 | Rapp |
| 2011/0297161 A1 | 12/2011 | Deitch |
| 2011/0301407 A1 | 12/2011 | Deitch |
| 2012/0108894 A1* | 5/2012 | Young ............... A61F 2/0045 600/37 |
| 2013/0281768 A1* | 10/2013 | Dolan ............... A61F 2/0045 600/37 |
| 2014/0275754 A1 | 9/2014 | Pereira et al. |
| 2014/0275755 A1* | 9/2014 | Pereira ............... A61F 2/0045 600/37 |
| 2015/0374474 A1 | 12/2015 | Hart et al. |
| 2016/0302788 A1 | 10/2016 | Pereira et al. |

FOREIGN PATENT DOCUMENTS

| | | |
|---|---|---|
| DE | 202014002429 U1 | 4/2014 |
| WO | 2003068107 A1 | 8/2003 |
| WO | 2003096929 A1 | 11/2003 |
| WO | 2004017845 A1 | 3/2004 |
| WO | 2004017862 A2 | 3/2004 |
| WO | 2004045457 A1 | 6/2004 |
| WO | 2005122954 A1 | 12/2005 |
| WO | 2006034719 A1 | 4/2006 |
| WO | 2006045042 A1 | 4/2006 |
| WO | 2006084167 A1 | 8/2006 |
| WO | 2006108145 A1 | 10/2006 |
| WO | 2007049154 A1 | 5/2007 |
| WO | 2007059199 A2 | 5/2007 |
| WO | 2007097994 A2 | 8/2007 |
| WO | 2007109759 A2 | 9/2007 |
| WO | 2007149348 A2 | 12/2007 |
| WO | 2007149555 A2 | 12/2007 |
| WO | 2007149593 A2 | 12/2007 |
| WO | 2009102945 A2 | 8/2009 |
| WO | 2010088917 A1 | 8/2010 |
| WO | 2011082350 A1 | 7/2011 |
| WO | 2012119145 A1 | 9/2012 |
| WO | 2014008130 A1 | 1/2014 |
| WO | 2014149612 A1 | 9/2014 |
| WO | 2015198352 A2 | 12/2015 |

\* cited by examiner

Y-SHAPED SACROCOLPOPEXY SUPPORT

BACKGROUND

Some women experience a reduction in the strength in the structure of the pelvic floor. A reduction in the strength of the pelvic floor muscles or in the supportive structure of the tissues in the pelvic floor can lead to the reduced support of one or more of the pelvic organs. Pelvic organs that have reduced support can prolapse, or descend, through the pelvic floor. This condition is referred to as pelvic organ prolapse. For example, rectocele refers to the prolapse of the anterior wall of the rectum downward and into the posterior wall of the vagina. Cystocele refers to the prolapse of the bladder downward and into the vagina. Vaginal prolapse refers to the prolapse of the cuff of the vagina downward through the vaginal opening, which can occur after removal of the uterus (or after removal of the uterus and the cervix). Sacrocolpopexy is a compound word that means fixation (pexy) of the vagina (colpo) to the sacrum or other sacral (sacro) tissue, usually with the aid of an implanted support. Sacralcolpopexy is synonymous with sacrocolpopexy.

SUMMARY

Embodiments provide a sacrocolpopexy support having a head section connected to a leg section. The head section is attachable to the sacrum or to ligaments attached to the sacrum and the leg section is attached to walls of the vagina. The head section is strong and suited for attachment to the sacrum. The leg section is supple and suited for attachment to the sensitive tissues of the vagina. The head section is formed from a material that has more weight and more strength than the leg section material. Embodiments described in this application provide a closed joint structure within the leg section that is configured to isolate or separate the heavier head section material away from the lighter weight leg section material that is attached to the sensitive vaginal tissues. Advantages of these embodiments include supporting the vagina with the more supple and lighter weight leg section of the support while anchoring the support to the tough tissue of the sacrum or the ligaments with the heavier weight material of the head section. Some advantages of the closed joint leg section structure include the reduction in the possibility of the heavier weight head section rubbing against the sensitive tissue of the vagina.

One embodiment provides a sacrocolpopexy support having a head section connected to a leg section. The head section extends from a first end portion to a second end portion. The leg section has a middle portion, a first leg portion extending from the middle portion to a first end of the leg section, and a second leg portion extending from the middle portion to a second end of the leg section. A fold is formed in the leg section such that the first leg portion is folded into contact with the second leg portion. A first connector connects the head section to the first leg portion, where the first connector is not coupled to the second leg portion. A second connector connects the first leg portion to the second leg portion, where the second connector is not coupled to the head section. The first connector is coupled through not more than two layers of the support, and the second connector is also coupled through not more than two layers of the support.

One embodiment provides a sacrocolpopexy support having a head section extending from a first end portion to a second end portion, and a leg section having a middle portion, a first leg portion extending from the middle portion to a first end of the leg section, and a second leg portion extending from the middle portion to a second end of the leg section. A fold is formed in the leg section such that the first leg portion is folded into contact with the second leg portion. A first connector secures the head section to the first leg portion and does not secure the head section to the second leg portion. A second connector secures the head section to the first leg portion and secures the head section to the second leg section. The first connector is coupled through not more than two layers of the support, and the second connector is coupled through three layers of the support.

One embodiment provides a sacrocolpopexy support having a head section connected to a leg section. The leg section has a first leg portion overlaying, or positioned atop, a second leg portion such that the first leg portion is arranged for attachment to an anterior wall of the vagina and the second leg portion is arranged for attachment to a posterior wall of the vagina. A connector connects the head section to the leg section, where the connector closes the first leg portion against the second leg portion to provide a closed joint that ensures that the head section is segregated away from the anterior and posterior walls of the vagina. In one embodiment, a single connector is employed to both connect the head section to the leg section and to close the first leg portion against the second leg portion.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
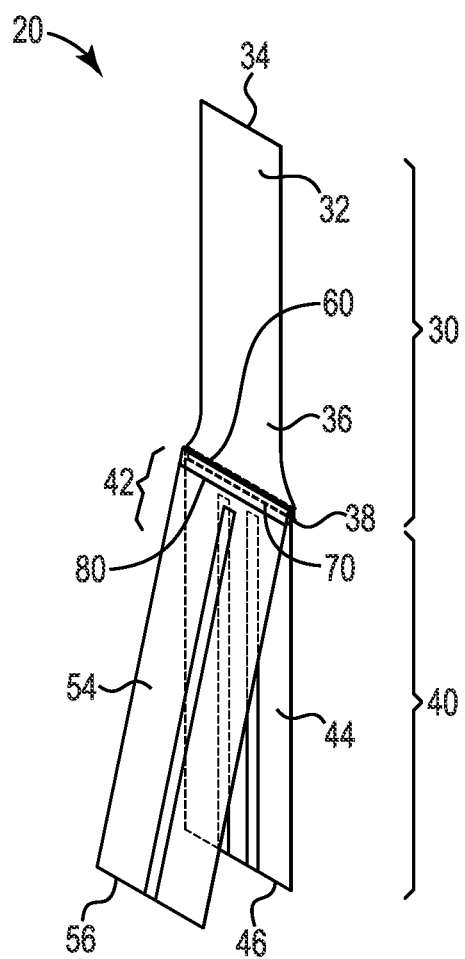
FIG. 1 is a perspective view of one embodiment of a sacrocolpopexy support.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The various exemplary embodiments described in this application may be combined with each other, unless specifically noted otherwise.

The term "proximal" in this application means that part that is situated next to or near the point of attachment or origin or a central point; for example, as located toward a center of the human body. The uterus is proximal relative to abdominal skin of the patient.

The term "distal" in this application means that part that is situated away from the point of attachment or origin or the central point; for example, as located away from the center of the human body. The abdominal skin is distal relative to the internal organs, such as the vagina or the uterus of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12-inch ruler has a center at 6 inches, a first end at zero inches and a second, opposite end at 12 inches, an end portion adjacent to the first end and another end portion adjacent to the second end.

The term "basis weight" means weight per area. One acceptable unit for basis weight is expressed as $g/m^2$.

A sacrocolpopexy support secures a prolapsed vaginal vault by anchoring or connecting the vaginal vault to one of the sacrum or ligaments associated with the sacrum. When the support is implanted, the previously prolapsed vaginal vault is supported or held up by the support that is connected between the tough sacrum/ligament tissues and the vagina. The sacrocolpopexy support described in this application has a head section connected to a leg section. The head section is attachable to the sacrum or to ligaments attached to the sacrum and the leg section is attached to walls of the vagina. The head section is strong and suited for holding the vagina in its anatomically correct position. The leg section is supple and suited for attachment to the sensitive tissues of the vagina. The head section is formed from a material that has more weight and more strength than the leg section material. Embodiments described in this application provide a closed joint structure within the leg section that is configured to isolate or separate the heavier head section material away from the lighter weight leg section material that is attached to the sensitive vaginal tissues. Some advantages of the closed joint leg section structure include the reduction in the possibility of the heavier weight head section rubbing against the sensitive tissue of the vagina. A first option in providing the leg section with a closed joint structure is to secure a first leg portion to the head section with a first connector, and then fold an integrated second leg portion over the first leg portion and then secure the second leg portion to the first leg portion and to the head section with a second connector. Thus, the leg section has one connector through the first leg portion and the head section and a second connector through second leg portion and the first leg portion and the head section. The second connector closes off the space between the first and second leg portions and maintains the endmost part of the head section out from the closed space of the leg section. A second option in providing the leg section with a closed joint structure is to secure a first leg portion to the head section with a first connector, and then fold an integrated second leg portion over the first leg portion and then secure the second leg portion to the first leg portion with a second connector. Thus, the leg section has one connector through the first leg portion and the head section and a second connector through second leg portion and the first leg portion and not through the head section. The second connector closes off the space between the first and second leg portions and maintains the endmost part of the head section behind the second connector and away from the closed space of the leg section. A third option in providing the leg section with a closed joint structure is to secure a first leg portion and a separate and individual second leg portion to the head section with a first connector, and then secure the second leg portion to the first leg portion with a second connector. Thus, the leg section has one connector through the first leg portion and the second leg portion and the head section and a second connector through second leg portion and the first leg portion and not through the head section. The second connector closes off the space between the first and second leg portions and maintains the endmost part of the head section behind the second connector and away from the closed space of the leg section. A fourth option in providing the leg section with a closed joint structure is to secure a first leg portion on one side and a separate and individual second leg portion to an opposite second side of the head section with a first connector, and then secure the second leg portion to the first leg portion with a second connector. The head section is located between the first leg portion and the second leg portion. Thus, the leg section has one connector through the first leg portion and the head section and the second leg portion, and a second connector through second leg portion and the first leg portion and not through the head section. The second connector closes off the space between the first and second leg portions and maintains the endmost part of the head section behind the second connector and away from the closed space of the leg section. Regarding these options, the first leg portion can be the same length as the second leg portion, such that a middle portion of the leg section is located equidistant between the first end and the second end of the leg section. Alternatively, the first leg portion can have a different length than the second leg portion. The connectors may be a polymer thread that is stitched to the materials, or an adhesive connection, or a thermal weld between polymer materials.

One embodiment of a sacrocolpopexy support has a head section connected to a leg section. The head section extends from a first end portion to a second end portion. The leg section has a middle portion, a first leg portion extending from the middle portion to a first end of the leg section, and a second leg portion extending from the middle portion to a second end of the leg section. A fold is formed in the leg section such that the first leg portion is folded into contact with the second leg portion. A first connector secures the head section to the first leg portion and does not secure the head section to the second leg portion. A second connector secures the head section to the first leg portion and secures the head section to the second leg section. In one embodiment, an end of the second end portion of the head section terminates at a location between the second connector and an end of the first and second leg portions.

Another embodiment of a sacrocolpopexy support has a head section extending from a first end portion to a second end portion, and a leg section having a middle portion, a first leg portion extending from the middle portion to a first end of the leg section, and a second leg portion extending from the middle portion to a second end of the leg section. A fold is formed in the leg section such that the first leg portion is folded into contact with the second leg portion. A first connector connects the head section to the first leg portion, where the first connector is not coupled to the second leg portion. A second connector connects the first leg portion to the second leg portion, where the second connector is not coupled to the head section.

Another embodiment of a sacrocolpopexy support has a head section extending from a first end portion to a second end portion, and a leg section having a first leg portion placed on and in longitudinal alignment with a second leg portion. A first connector secures the leg section to the second end portion of the head section. The first connector secures at least one of the leg portions of the leg section to the second end portion of the head section. A second connector secures the first leg portion to the second leg portion. The second connector is not coupled to the head section, and an end of the second end portion of the head section terminates at and is located between the first connector and the second connector.

Another embodiment of a sacrocolpopexy support has a head section extending from a first end portion to a second end portion and a leg section having a first leg portion placed on and in longitudinal alignment with a second leg portion. A first connector secures the leg section to the second end portion of the head section. A second connector secures the first leg portion to the second leg portion to form a closed joint that defines a space between the first leg portion and the second leg portion. An end of the second end portion of the head section terminates at a location exterior to the closed joint outside of the space between the first leg portion and the second leg portion. One embodiment of this sacrocolpopexy support provides the leg section with a middle portion, with the first leg portion extending from the middle portion to a first end of the leg section and the second leg portion extending from the middle portion to a second end of the leg section; a fold is formed in the middle portion of the leg section such that the first leg portion is folded into contact with the second leg portion; the first connector is connected through the first leg portion and the second end portion of the head section and not connected to the second leg portion, and the second connector is connected through the first leg portion, the second end portion of the head section, and the second leg portion. One embodiment of this sacrocolpopexy support provides the leg section as a single integrated material with the first leg portion extending from and connected to the second leg portion, and a fold is formed in the leg section such that the first leg portion is folded into contact with the second leg portion; the first connector is connected through the first leg portion and the second end portion of the head section and not connected to the second leg portion, and the second connector is not coupled to the head section; an end of the second end portion of the head section terminates at and is located between the first connector and the second connector. One embodiment of this sacrocolpopexy support provides the first leg portion as separate from the second leg portion, with the first leg portion longitudinally aligned and in contact with the second leg portion; the first connector is connected through the first leg portion, the second leg portion, and the second end portion of the head section; the second connector is not coupled to the head section; an end of the second end portion of the head section terminates at and is located between the first connector and the second connector. One embodiment of this sacrocolpopexy support provides the first leg portion as separate from the second leg portion, with the first leg portion longitudinally aligned with the second leg portion and the second end portion of the head section is disposed between the first leg portion and the second leg portion; the first connector is connected through the first leg portion, the second end portion of the head section, and the second leg portion; the second connector is not coupled to the head section; an end of the second end portion of the head section terminates at and is located between the first connector and the second connector.

Another embodiment of a sacrocolpopexy support has a head section extending from a first end portion to a second end portion, and a leg section that is folded upon itself to provide a first leg portion and a second leg portion. One or more connectors are employed to secure the leg section to the second end portion of the head section. In one embodiment, three or more connectors are employed to secure the leg section to the head section.

The sacrocolpopexy support is Y-shaped, where the first leg portion and the second leg portion combine to provide a V-shape and the head section is attached to the leg portions to form a combined Y-shape. When the sacrocolpopexy support is implanted, the head section is connected to the sacrum or sacral tissue, and the V-shape of the leg section engages the vagina with the first leg portion connected to the anterior wall of the vagina and the second leg portion connected to the posterior wall of the vagina. The advantage provided by the configurations described in this application is that the head section is spaced apart from and kept away from contacting the sensitive tissue of the vagina. A connector is provided to close the V-shape of the leg portions together in a way that maintains the end of the head section outside of the V-shape. The head section connected to the sacrum is generally coarser, stronger, and tougher than the leg section. It is desirable to prevent the head section from contacting the tissue of the vagina, as this could potentially lead to erosion of the vaginal tissue. The fold of the leg section, in combination with the first and second connector locations, ensures that only the softer leg section interacts with the delicate tissue of the vagina. In contrast, some supports have first leg attached to a first side of the head section and a second leg attached to a second side of the head section, which leaves the head section between the legs and located to possibly abrade the delicate tissue of the vagina.

Again, in contrast, some supports provide one long head section (or tail) that extends from the sacrum to the vagina and a shorter leg section is attached to the head section, which also locates the heavier and stiffer head section in contact with the vagina.

In one embodiment, the head section has an anterior side opposite of a posterior side, and the first leg portion and the second leg portion are both located on only the anterior side of the head section. This configuration has the advantage of locating the leg section material for attachment to both sides of the vagina while also isolating the head section material away from the tissue of the vagina.

In one embodiment, the leg section is a single integrated piece of material with the middle portion located equidistant between the first end of the leg section and the second end of the leg section. This configuration has the advantage of providing the surgeon with a symmetrical leg section, so the surgeon does not have to spend time deciding "which end is up." The surgeon may, of course, choose to trim or cut the first and second leg portions to different lengths.

In one embodiment, the leg section is a rectangle defined by a leg section length and a leg section width, and the first connector and the second connector are connected to the second end portion of the head section, with a width of the second end portion of the head section that is equal to the leg section width and is larger than a width of the first end portion of the head section. This configuration has the advantage of providing more width to the leg section, which aids the surgeon in the attachment of the leg section to the wall of the vagina and also provides excellent vaginal support. The narrower head section allows the surgeon to more easily pass the narrow end of the head section under the peritoneum for connection to the sacrum.

In one embodiment, the first connector is closer to the fold than the second connector is to the fold. This configuration has the advantage of locating the second connector farther from the fold compared to the first connector, which forms a vertex with leg section material on both sides of the vertex. When the leg section is connected to the tissue of the vagina, the vertex locates leg section material on either side of the vagina and isolates the head section material away from the tissue of the vagina.

In one embodiment, the first connector is a suture that is stitched through not more than two layers of material of the sacrocolpopexy support. This configuration has the advantage of allowing the third layer of material (the second leg portion) to fold over the first connector to provide a vertex of leg material that engages with the vagina, while also isolating the head section material away from the tissue of the vagina.

In one embodiment, the second connector is a suture that is stitched through three layers of material of the sacrocolpopexy support. This configuration has the advantage of forming a vertex of leg material that engages with the vagina, while also isolating the head section material away from the tissue of the vagina.

In one embodiment, a length of the first leg portion measured from the fold to the first end of the leg section is equal to a length of the second leg portion measured from the fold to the second end of the leg section. This configuration has the advantage of providing a symmetric leg portion.

In one embodiment, a distance measured from the second connector to the first end of the leg section is equal to a distance measured from the second connector to an end of the first end portion of the head section. This configuration has the advantage of providing a symmetric support with equal parts of a leg section attachable to the vagina and head section.

In one embodiment, a transverse width of the leg section is greater than a transverse width of the first end portion of the head section. This configuration has the advantage of providing a smoothly tapered and narrower head section.

In one embodiment, a basis weight of the leg section is less than 30 g/m$^2$, which advantageously provides a light weight support structure for attachment to the delicate tissue of the vagina.

In one embodiment, a basis weight of the first leg portion is equal to a basis weight of the second leg portion, which advantageously provides a uniform support structure for attachment to the delicate tissue of the vagina.

In one embodiment, a basis weight of the leg section is less than 30 g/m$^2$ and a basis weight of the head section is greater than 30 g/m$^2$, which advantageously provides a light weight support structure for attachment to the delicate tissue of the vagina and a heavier support for connection to the tough sacral tissue.

In one embodiment, a single line is printed in ink on the first leg portion and is located longitudinally on a longitudinal center of the first leg portion to advantageously provide a guide or index that allows the surgeon to center the leg section relative to a wall of the vagina.

In one embodiment, a first line is printed in ink on the second leg portion and a second line is printed in ink on the second leg portion, with each of the first line and the second line located longitudinally on the second leg portion and offset away from a longitudinal center of the second leg portion. This configuration has the advantage of distinguishing the second leg portion from the first leg portion, while also providing the surgeon with a center location between the two printed lines.

Embodiments provide a sacrocolpopexy support having a head section connected to a leg section. The head section extends from a first end portion to a second end portion. The leg section has a middle portion, a first leg portion extending from the middle portion to a first end of the leg section, and a second leg portion extending from the middle portion to a second end of the leg section. A fold is formed in the middle portion of the leg section, with the middle portion of the leg section connected to the head section. The head section has an anterior side opposite of a posterior side, and in an embodiment both of the first leg portion and the second leg portion are located on only the anterior side of the head section.

Embodiments provide a sacrocolpopexy support having a leg section connected to a head section. The head section is knitted with a monofilament polypropylene fiber into a knit structure having a weight per area in a range from 30-50 g/m$^2$. The leg section is knitted with a monofilament polypropylene fiber into a knit structure having a weight per area in a range from 17-29 g/m$^2$, with the leg section having a first leg portion overlaying a second leg portion. A first connector connects the first leg portion to the second leg portion to form a closed space located between the first leg portion and the second leg portion. An entirety of the head section is located outside of the closed space located between the first leg portion and the second leg portion.

In one embodiment, the head section is located on a proximal side of the sacrocolpopexy support and the leg section is located on a distal side of the sacrocolpopexy support, and the entirety of the head section is located proximal relative to the first connector. This configuration provides the advantage of keeping the head section out of the closed space located between the first leg portion and the second leg portion. When implanted, the vagina is located within the closed space located between the first leg portion and the second leg portion, and thus the head section is isolated away from the sensitive tissues of the vagina.

FIG. 1 is a perspective view of one embodiment of a sacrocolpopexy support 20 (support 20). The support 20 includes a head section 30 connected to a leg section 40. The head section 30 is attached to the sacrum or its adjacent tissues during implantation and the leg section 40 is attached to an exterior wall of the vagina. The head section 30 is suitably attached to the bony sacrum or the soft tissues covering the bony sacrum or the connective tissues, such as ligaments, extending from the sacrum. Sutures, staples, or tacks, depending upon the preference of the surgeon, may be employed to secure the head section 30 to the sacral tissue. The leg section 40 is generally secured to an exterior surface of both the anterior wall and the posterior wall of the vagina, for example through the use of sutures.

The head section 30 has a first end portion 32 terminating in a first end 34 and a second end portion 36 terminating in a second end 38.

The leg section 40 has a middle portion 42, a first leg portion 44 extending from the middle portion 42 to a first end 46, and a second leg portion 54 extending from the middle portion 42 to a second end 56. The first leg portion 44 and the second leg portion 54 are connected to the head section 30.

A portion of the leg section 40 is connected to the head section 30, and a fold 60 is formed in the leg section 40 to place the second leg portion 54 over the first leg portion 44. The leg section 40 is a single integrated piece of material with the middle portion 42 located between the first end 46 and the second end 56 of the leg section 40. The fold 60 can be folded in a manual procedure by hand, or in an automated procedure by machine prior to securing the leg section 40 to the head section 30, or after first securing a part of the leg section 40 to part of the head section 30. In one embodiment, the first leg portion 44 is the same length as the second leg portion 54, such that the middle portion 42 is located equidistant between the first end 46 and the second end 56 of the leg section 40. In one embodiment, the first leg portion 44 has a different length than the second leg portion 54.

A first connector 70 secures the head section 30 to the first leg portion 44, and a second connector 80 secures the head section 30 to the first leg portion 44 and the second leg portion 54. Suitable connectors for the first connector 70 and the second connector 80 include a polymer strand that is stitched through portions of the support 20, ultrasonically welded lines, segments of glue, or combinations of glue and sutures. In one embodiment, the first connector 70 and the second connector 80 are provided by a polypropylene monofilament strand that is stitched through portions of the head section 30 and the leg section 40.

The support 20 is selected to be bio-compatible with implantation into a human body and is configured to allow tissue to grow through the head section 30 and the leg section 40 to anchor the support 20 in the body after implantation and healing. Suitable materials for the support 20 include autograft material (the patient's own tissue), allograft material (tissue from a cadaver), xenograft material (tissue from another species), or synthetic materials such as knitted meshes, woven fabrics or meshes, nonwoven fabrics or meshes, fibrillated fibers, or spun and fibrillated fibers. The support 20 is provided with voids including major spaces and smaller pores. The voids allow tissue ingrowth into and through the support 20. The major spaces have a size in a range from 1-10 mm and the pores have a size in a range from 50-200 µm.

In one embodiment, the support 20 is a knitted monofilament polypropylene mesh with the head section 30 provided with a heavier weight per area than the leg section 40.

One suitable head section 30 is knitted with a 100 µm monofilament polypropylene fiber into a knit structure having a thickness in a range from 0.3-0.5 mm and a weight per area in a range from 30-50 g/m$^2$, and preferably with a weight per area of approximately 34 g/m$^2$. Other fibers formed from other material and having a diameter different from the 100 µm monofilament polypropylene fiber are also acceptable. For example, fiber having a 90 µm or a 120 µm diameter is acceptable.

One suitable leg section 40 is knitted with an 80 µm monofilament polypropylene fiber into a knit structure having a thickness in a range from 0.25-0.36 mm and a weight per area in a range from 17-29 g/m$^2$, and preferably with a weight per area of approximately 22 g/m$^2$. Other fibers formed from other material and having a diameter different from the 80 µm monofilament polypropylene fiber are also acceptable. For example, fiber having a 70 µm or a 90 µm diameter is acceptable. In one embodiment, the leg section 40 is provided as a rectangle that is folded on a line about fold 60 such that the weight per area of the first leg portion 44 is equal to the weight per area of the second leg portion 54.

The leg section 40 mesh is thin and light weight (i.e., the weight per area or basis weight is less than approximately 30 g/m$^2$) to provide a thin and comfortable mesh that is agreeable with the delicate vaginal tissue that contacts the mesh and is less likely to be sensed through the tissue layers by the patient.

The embodiments of the support provide a structure that keeps the heavier material of the head section 30 separated away from the sensitive tissue of the vagina. This is achieved by locating the heavier weight material of the head section 30 away from where the light weight material of the leg section 40 is attached (or attachable) to the vagina.

Suitable knitted monofilament polypropylene mesh is available from Coloplast Corp., Minneapolis, MN.

Figure 2:
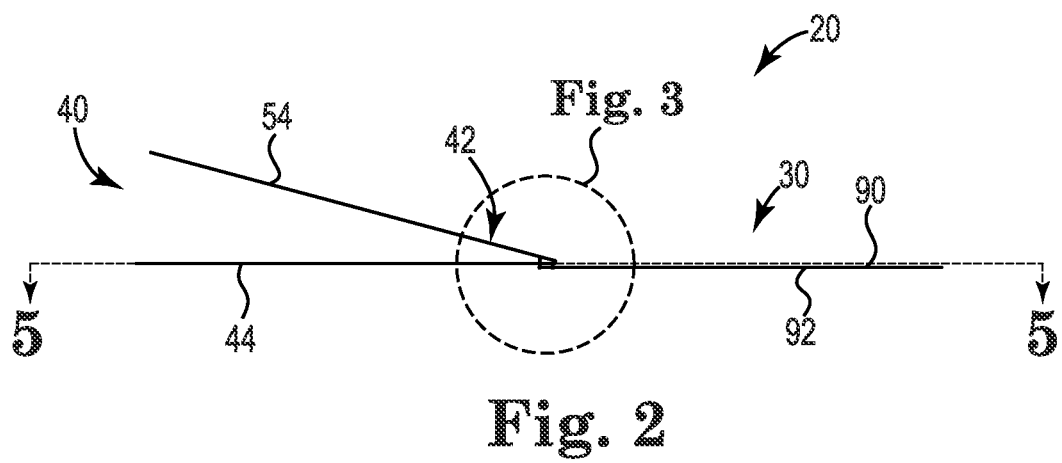
FIG. 2 is a right side view of the sacrocolpopexy support illustrated in FIG. 1.
Figure 3:
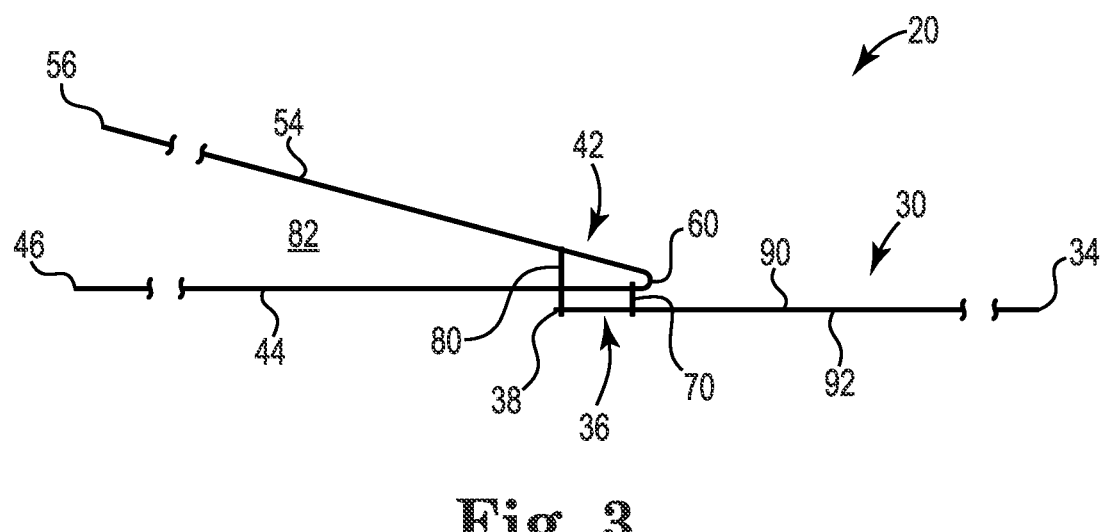
FIG. 3 is a right side view of showing a connector between a leg section and a head section of the sacrocolpopexy support.

FIG. 2 is a right side view of the support 20 and FIG. 3 is a view of the connectors 70, 80 securing the head section 30 to the leg section 40.

The fold 60 is formed in the middle portion 42 of the leg section 40. The first connector 70 secures the head section 30 to the first leg portion 44 but does not secure the head section 30 to the second leg portion 54. That is to say, the first connector 70 extends through the head section 30 and only the first leg portion 44 and does not extend through the second leg portion 54. The first connector 70 is coupled to the head section 30 and only the first leg portion 44 and is not coupled to the second leg portion 54. The second connector 80 secures the head section 30 to both the first leg portion 44 and the second leg portion 54.

The leg section 40 and the head section 30 combine to provide a Y-shaped support when viewed from a side edge of the sacrocolpopexy support 20, as illustrated in FIGS. 1-3. The Y-shaped support 20 has a V-shaped portion formed by the first leg portion 44 and the second leg portion, and the head section 30 is attached to the V-shaped portion to complete the Y-shaped conformation. When implanted, the V-shape of the leg section 40 engages the vagina with the first leg portion 44 connected to the anterior wall of the vagina and the second leg portion 54 connected to the posterior wall of the vagina. The head section 30 is spaced apart from and kept out of the interior of the V-shaped portion of the leg section 40. Specifically, the second connector 80 has closed the V-shaped portion at its apex area. This configuration ensures that the head section 30 is kept away from contacting the sensitive tissue of the vagina since the head section 30 is maintained outside of the V-shaped portion of the leg section 40.

In one embodiment, the connector 80 connects the first leg portion 44 to the second leg portion 54 to form a closed space 82 located between the first leg portion 44 and the second leg portion 54, and an entirety of the head section 30 is located outside of the closed space 82 located between the first leg portion 44 and the second leg portion 54.

In one embodiment, the head section 30 has an anterior side 90 opposite of a posterior side 92, and the connectors 70, 80 secure the folded leg section 40 to only one of the anterior side 90 or the posterior side 92 of the head section 30. In the exemplary embodiment illustrated in FIGS. 2 and 3, the first leg portion 44 and the second leg portion 54 are both located on only the anterior side 90 of the head section 30.

With regard to the attachment, the first connector 70 is coupled to not more than two layers of material of the support 20 and second connector 80 is coupled to at least three layers (head section 30 and both leg portions 44, 54) of material of the support 20. For example, the first connector 70 is a suture that is stitched through not more than two layers of material of the support 20 and the second connector 80 is a suture that is stitched through three layers, or more than three layers, of material of the support 20. One suitable connector material is polypropylene monofilament, for example, an 80 µm monofilament polypropylene fiber. In one embodiment, the first connector 70 is separate and distinct from the second connector 80. In one embodiment, the first connector 70 and the second connector 80 are formed by a sewn pattern that provides both connectors 70, 80 where the first connector 70 extends through the head section 30 and only the first leg portion 44 and does not extend through the second leg portion 54 and the second connector 80 secures the head section 30 to both the first leg portion 44 and the second leg portion 54. In one embodiment, each of the connectors 70, 80 is formed by an interlocking stitch that is stitched across the full width of the head section 30 and the leg section 40. The interlocking stitch is placed in a transverse direction, preferably parallel with the second end 38 of the head section 30.

The first connector 70 and the second connector 80 fixate the middle portion 42 of the leg section 40 to the second end portion 36 of the head section 30. The first connector 70 is closer to the fold 60 than the second connector 80 is to the fold 60, which is to say that the second connector 80 is closer to the second end 38 of the head section 30 than the first connector 70 is to the second end 38 of the head section 30. In one embodiment, a length of the first leg portion 44 measured from the fold 60 to the first end 46 is equal to a length of the second leg portion 54 measured from the fold 60 to the second end 56 of the leg section 40.

It is acceptable to secure the leg section 40 to the head section 30 by, for example, securing first leg portion 44 to the head section 30 with adhesive or by thermal welding of the materials, and then to place a single mechanical connector, such as stitch line 80 or adhesive or thermal welding, to secure the first leg portion 44 to the second leg portion 54, where the single connector closes the leg section 40 and isolates the end 38 of the head section 30 outside of the closed space formed between the leg portions 44, 54.

Figure 4A:
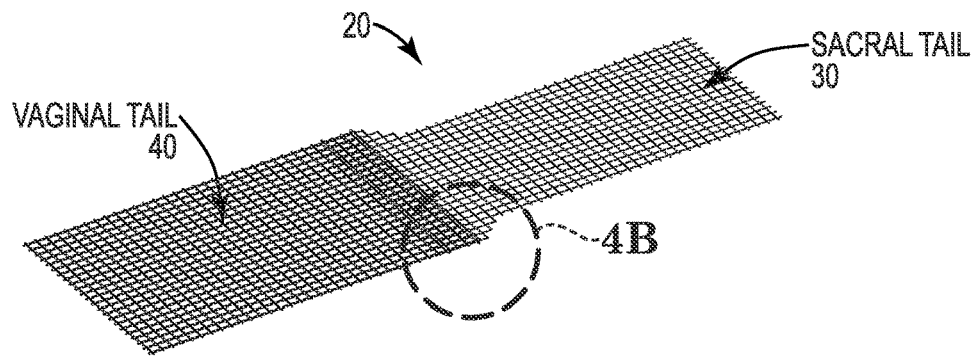
FIG. 4A and FIG. 4B are perspective views and FIG. 4C is a side schematic view of the leg section connected to the head section.
Figure 4B:
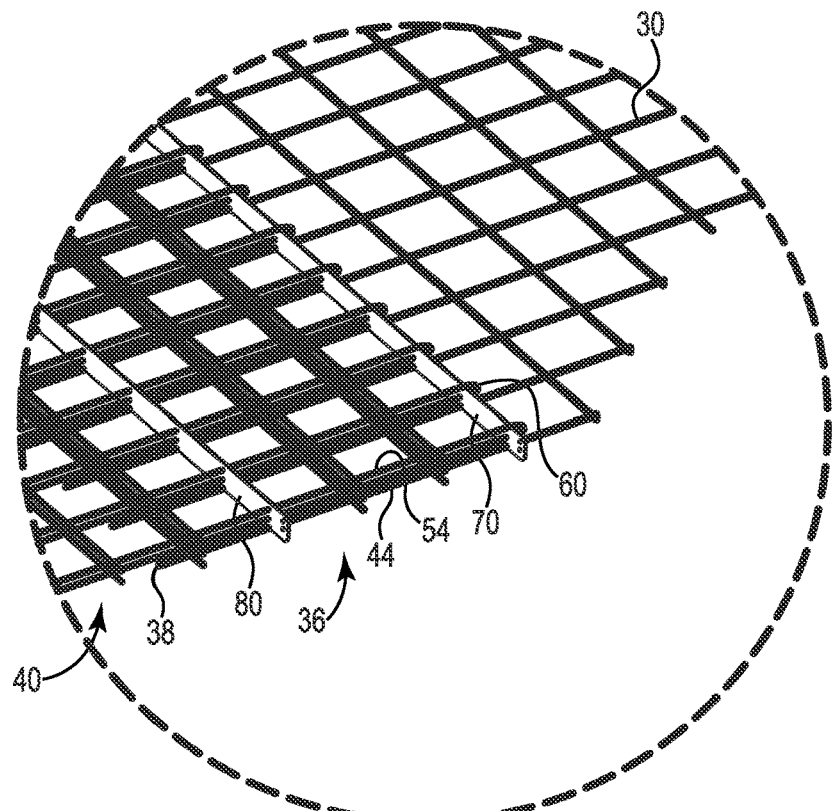
Figure 4C:
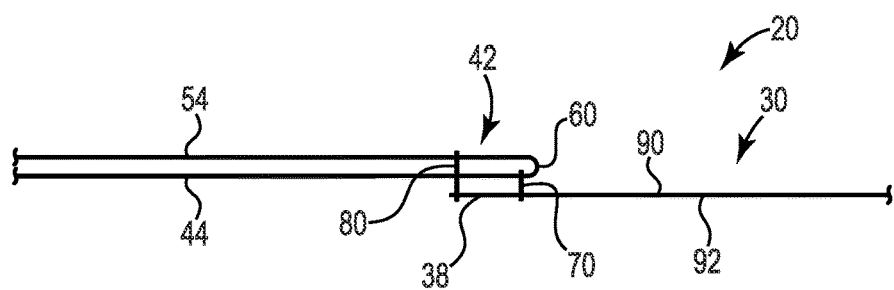

FIG. 4A and FIG. 4B are a top perspective views and FIG. 4C is a side schematic view of the first connector 70 and the second connector 80 securing the head section 30 to the leg section 40.

The first connector 70 and the second connector 80 combine to provide what is termed a closed joint construction that separates the vaginal attachment portions of the lightweight structure of the leg section 40 away from the heavier structure of the head section 30. The closed joint construction is provided by aligning the open pores or open holes of the first leg portion 44 with the open holes of the head section 30 and then stitching a monofilament fiber through the open holes of the first leg portion 44 and the head section 30 to provide the first connector, which is illustrated by the dotted line 70 since this stitch pattern would be covered over by the second leg portion 54 (and thus not visible from above). A separate second stitch, spaced apart from the first stitch of connector 70, is passed through the aligned open holes of the first leg portion 44, the second leg portion 54, and the head section 30 to provide the second connector 80, which is illustrated by the solid line 80 since this stich goes through all three layers and is visible from above and below.

The stitches of the first and second connectors 70, 80 are formed in a path along a width of the support 20 in the aligned holes of the leg section 40 and the head section 30. In one embodiment, each stitch is formed in two passes, first in one direction across a width the support 20 and then in a reversed, second path across the width support 20. The advantage of a two-pass stitch pattern is realized in that twice-stitched closed joint resists separation when the support 20 is trimmed or cut. The two-pass stitch pattern forms a strong joint that allows the surgeon to cut the support 20 without the undesirable consequence of the leg section 40 separating from the head section 30.

In the illustrated embodiment, the head section 30 has an anterior side 90 opposite of a posterior side 92, and the first leg portion 44 and the second leg portion 54 are both located on only the anterior side 90 of the head section 30. This configuration contributes to the keeping the heavier structure of the head section 30 away from the sensitive tissue of the vagina that is supported by and attached to the lightweight structure of the leg section 40.

Figure 5:
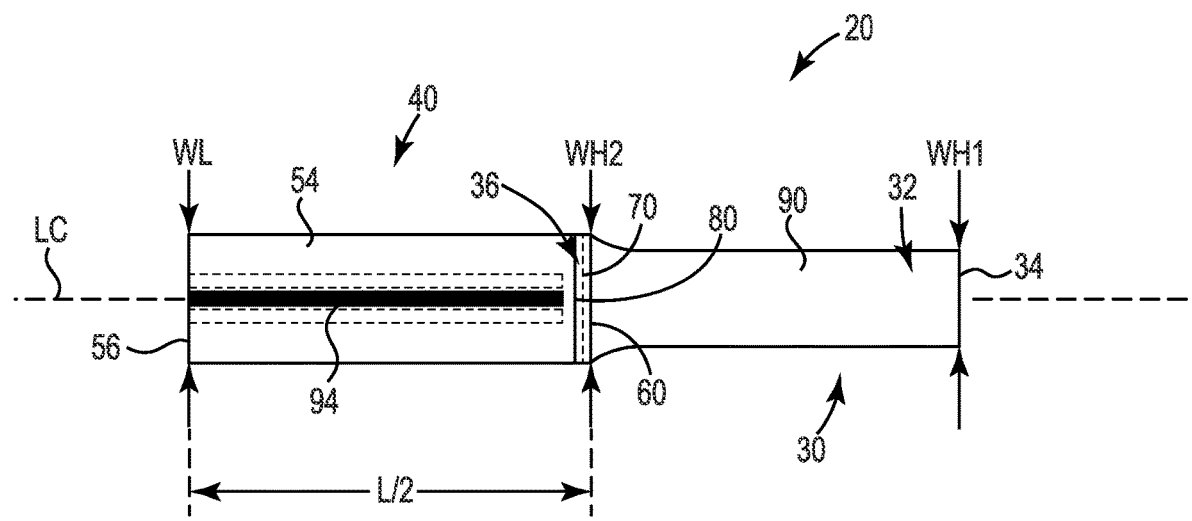
FIG. 5 is a front side view of the sacrocolpopexy support illustrated in FIG. 1.
Figure 6:
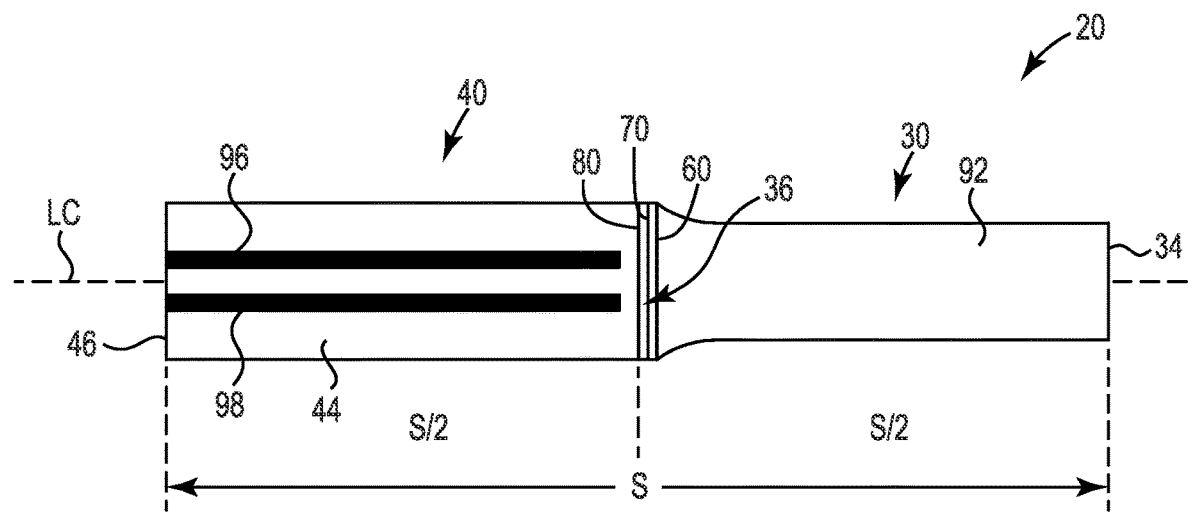
FIG. 6 is a back side view of the sacrocolpopexy support illustrated in FIG. 1.

FIG. 5 is a front view of the support 20 and FIG. 6 is a back view of the support 20. FIG. 5 is thus a view of the second leg portion 54 and FIG. 6 is a view of the first leg portion 44.

The leg section 40 has a leg section length L and a leg section width WL (thus, the first leg portion 44 and the second leg portion 54 each have a length of L/2). The leg section 40 is folded at the fold 60 (See FIG. 3). The first connector 70 and the second connector 80 are connected to the second end portion 36 of the head section 30. A width WH2 of the second end portion 36 of the head section 30 is equal to the leg section width WL and is larger than a width WH1 of the first end portion 32 of the head section 30. In this manner, the head section 30 diverges from a narrower width WH1 at the first end 34 to a wider width WH2 at the second end section 36, and the width WH2 is equal to the width WL of the leg section 40. Thus, a transverse width of the leg section 40 (WL) is greater than a transverse width of the first end portion 32 of the head section 30 (WH1).

In one embodiment, the support 20 is configured such that a distance S/2 measured from the second connector 80 to the first end 46 of the leg section 40 is equal to a distance S/2 measured from the second connector 80 to the end 34 of the head section 30. The total length of the support 20 is S (S/2 plus S/2).

In one embodiment, the support 20 has a single line 94 printed in ink on the second leg portion 54, with the single line 94 located longitudinally on a longitudinal center LC of the second leg portion 54.

In one embodiment, the support 20 has dual lines printed on the first leg portion. For example, a first line 96 is printed in ink on the first leg portion 44 and a second line 98 is printed in ink on the first leg portion 44, with each of the first line 96 and the second line 98 located longitudinally on the first leg portion 44 and offset away from the longitudinal center LC of the support 20 and the first leg portion 44.

The printed lines provide a guide to allow the surgeon to place the leg section 40 in a desired orientation. The printed lines are an optional feature for the support 20.

Figure 7:
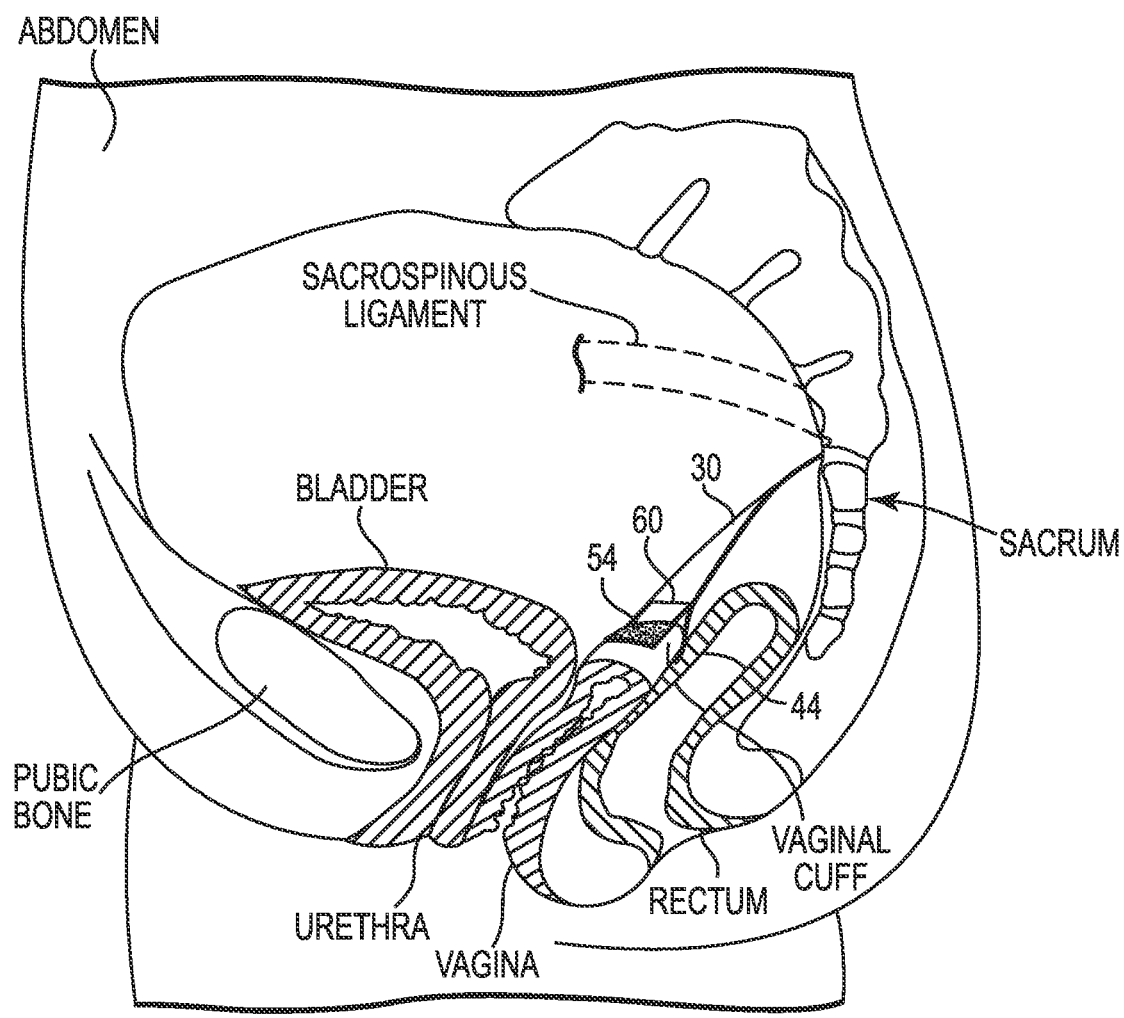
FIG. 7 is a schematic view of the sacrocolpopexy support illustrated in FIG. 1 implanted in a patient.

FIG. 7 is a schematic perspective view of the sacrocolpopexy support 20 implanted in a patient.

One acceptable procedure for implanting the support 20 into the patient is a trans-abdominal laparoscopic procedure. Some healthcare facilities employ robotically assisted laparoscopic procedures. During the trans-abdominal laparoscopic procedure, access ports (trocars) are placed in the abdomen of the patient. The laparoscope is inserted through one of the trocars into the abdomen for access to the vaginal cuff. An inert gas is pumped into a second of the trocars to inflate the abdominal region for improved access and viewing of the pelvic organs. The surgeon will often position the vagina by inserting a supporting device (sometimes referred to as a manipulator) into the natural vaginal opening to orient the vaginal cuff to a desired position suited for viewing of the vaginal cuff when attaching the support 20. Other surgical procedures are also acceptable, depending upon surgeon preference.

The support 20 is inserted through a trocar. The head section 30 is secured to the sacrum and the leg section 40 is secured to the vaginal cuff. In the illustration of FIG. 7, the second leg portion 54 has been attached to the anterior wall of the vagina and the first leg portion 44 has been attached to the posterior wall of the vagina. It is also acceptable to attach the head section 30 the sacrospinous ligament, depending upon the preference of the surgeon.

Figure 8:
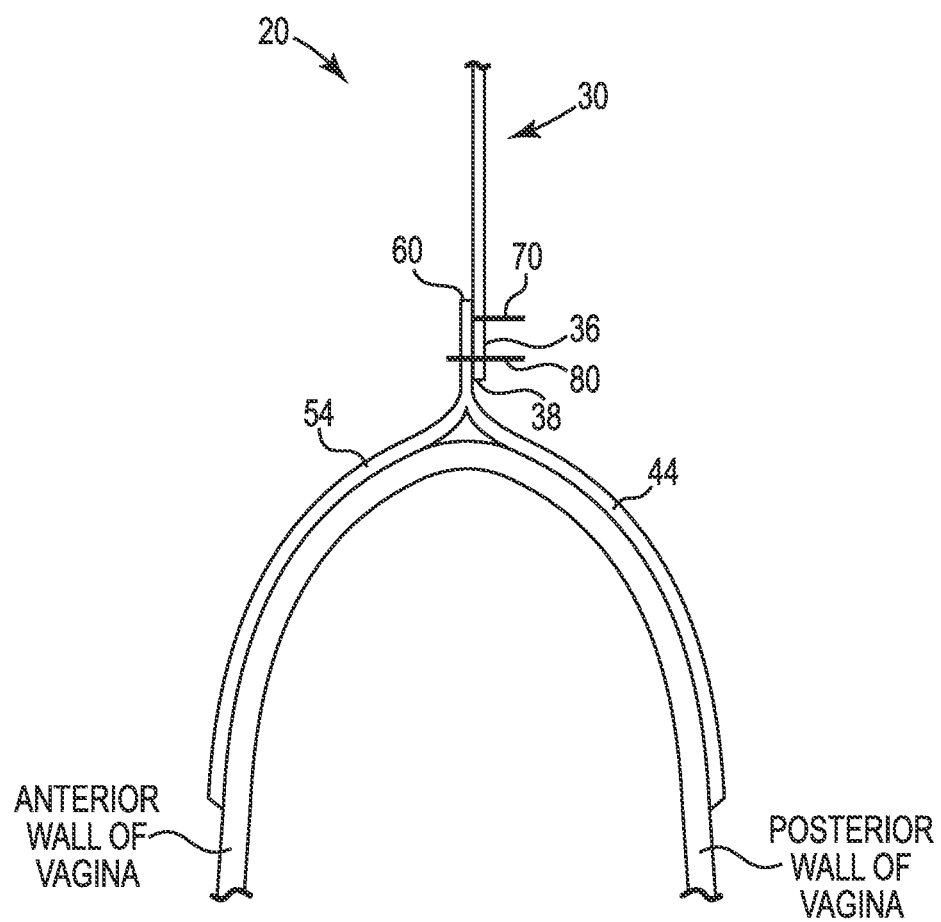
FIG. 8 is a schematic side view of the sacrocolpopexy support illustrated in FIG. 1 secured to a vagina of the patient.

FIG. 8 is a schematic side view of the sacrocolpopexy support 20 secured to a vagina of a patient. The head section 30 extends superiorly to the where it is attached to the sacrum and the leg section 40 extends inferiorly where it is attached to the cuff of the vagina. The first leg portion 44 has been secured to the posterior wall of the vagina and the second leg portion 54 has been secured to the anterior wall of the vagina. Suitable securement devices such as sutures or staples are employed for fixation, depending upon the preference of the surgeon. The fold 60 in combination with the connectors 70, 80 and their locations combine to ensure that lighter weight material of the leg portions 44, 54 are the only portion of the support 20 that is in contact with the delicate tissue of the vagina. The head section 30, fabricated from a heavier material than the leg section, is isolated and separated away from the delicate tissue of the vagina.

Exemplary Performance Data

Sacrocolpopexy supports were fabricated and evaluated. The supports each have a head section and a leg section, and Table 1 below illustrates the physical properties of each of these portions of the support. The physical properties recited in Table 1 provide one example of performance characteristics for use as a sacrocolpopexy support in the treatment of pelvic organ prolapse.

TABLE 1

| Property | Head Section | Leg Section |
| --- | --- | --- |
| Suture pull | ≥11.6N | ≥8.7N |
| Tensile strength 2 cm width | ≥33.8N | ≥20.9N |
| Tear strength | ≥6.2N | ≥4.3N |
| Bending length 2 cm width | ≤36.5 mm | ≤36.5 mm |
| Density | 30-34.0 g/m$^2$ | ≤22.62 g/m$^2$ |
| Thickness | 0.013-0.019 in | 0.011-0.014 in |
| Ball burst strength | ≥28.0N | ≥13.1N |
| Large pore length | 1.8-2.2 mm | 1.8-2.2 mm |
| Small pore dimension | ≥75 μm | ≥75 μm |

Figure 9:
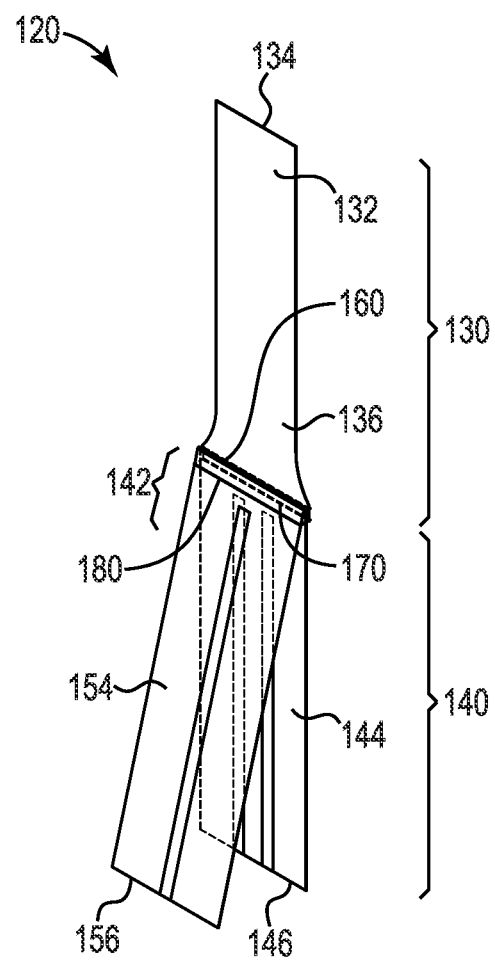
FIG. 9 is a perspective view of one embodiment of a sacrocolpopexy support.

FIG. 9 is a perspective view of another embodiment of a sacrocolpopexy support 120 (support 120).

The support 120 includes a head section 130 connected to a leg section 140. The head section 130 is attached to the sacrum or its adjacent tissues during implantation and the leg section 140 is attached to an exterior wall of the vagina. The head section 130 is suitably attached to the bony sacrum or the soft tissues covering the bony sacrum or the connective tissues, such as ligaments, extending from the sacrum. Sutures, staples, or tacks, depending upon the preference of the surgeon, may be employed to secure the head section 130 to the sacral tissue. The leg section 140 is generally secured to an exterior surface of both the anterior wall and the posterior wall of the vagina, for example through the use of sutures.

Figure 10:
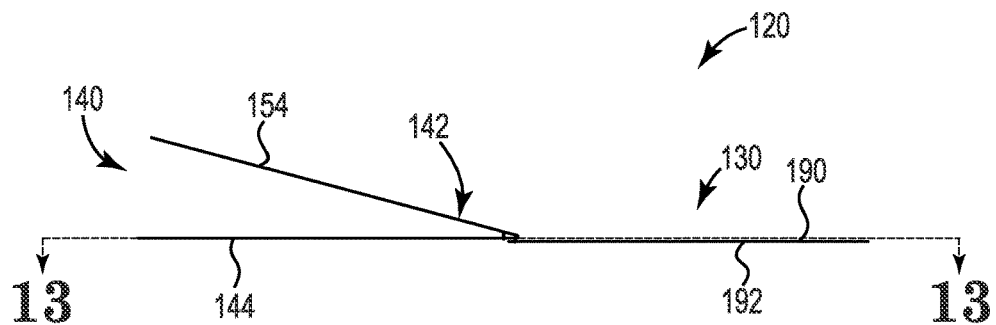
FIG. 10 is a right side view of the sacrocolpopexy support illustrated in FIG. 9.
Figure 11A:
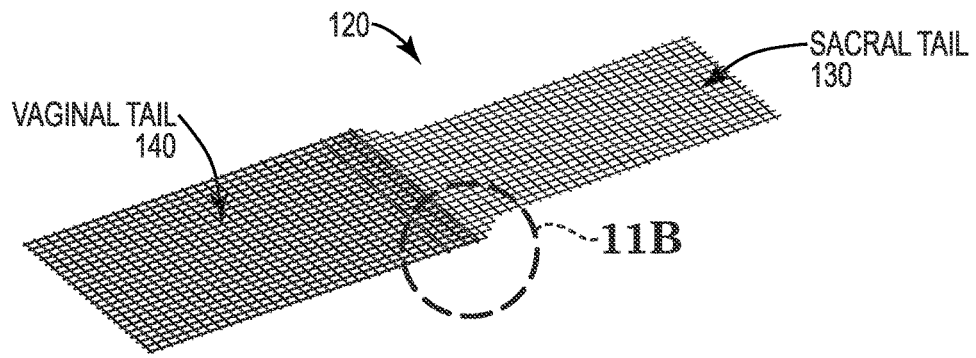
FIG. 11A and FIG. 11B are perspective views of a leg section connected to a head section of the sacrocolpopexy support.
Figure 11B:
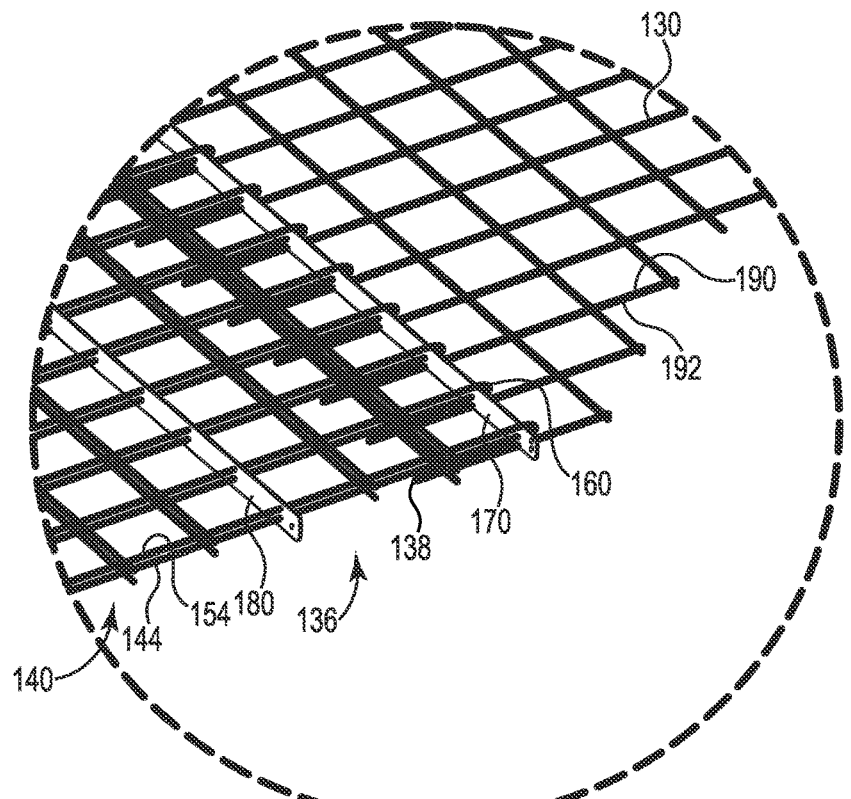

FIG. 10 is a right side view and FIGS. 11A and 11B are perspective views of the support 120.

The head section 130 has a first end portion 132 terminating in a first end 134 and a second end portion 136 terminating in a second end 138.

The leg section 140 has a middle portion 142, a first leg portion 144 extending from the middle portion 142 to a first end 146, and a second leg portion 154 extending from the middle portion 142 to a second end 156.

A first connector 170 secures the head section 130 to the first leg portion 144, and a second connector 180 secures the first leg portion 144 to the second leg portion 154 and is not coupled through the head section 130. Suitable connectors for the first connector 170 and the second connector 180 include a polymer strand that is stitched through portions of the support 120, ultrasonically welded lines, segments of glue, or combinations of glue and sutures. In one embodiment, the first connector 170 and the second connector 180 are provided by an 80 μm monofilament polypropylene fiber.

This embodiment of a sacrocolpopexy support 120 has a head section 130 extending from a first end portion 132 to a second end portion 136, and a leg section 140 having a first leg portion 144 placed on and in alignment with a second leg portion 154. A first connector 170 secures the leg section 140 to the second end portion 136 of the head section 130. A second connector 180 secures the first leg 144 portion to the second leg portion 154. The second connector 180 is not coupled to the head section 130, and an end 138 of the second end portion 136 of the head section 130 terminates at and is located between the first connector 170 and the second connector 180.

In one embodiment, a fold 160 is formed in the leg section 140 such that the first leg portion 144 is folded into contact with the second leg portion 154. The leg section 140 is a single integrated piece of material with the middle portion 142 located between the first end 146 and the second end 156 of the leg section 140. In one embodiment, the leg section 140 is provided as a rectangle that is folded on a line about fold 160 such that the weight per area of the first leg portion 144 is equal to the weight per area of the second leg portion 154. The fold 160 can be folded in a manual procedure by hand or in an automated procedure by machine prior to securing the leg section 140 to the head section 130. In an exemplary embodiment, the first connector 170 is placed to secure the first leg portion 144 to the head section 130, and the second leg portion 154 is folded to overlay the first leg portion 144 prior to securing the first leg portion 144 to the second leg portion 154 with the connector 180.

In one embodiment, the first leg portion 144 is placed on top of the second leg portion 154 and these components are not folded as an integral piece of material.

It is acceptable to secure the leg section 140 to the head section 130 by, for example, securing first leg portion 144 to the head section 130 with adhesive or by thermal welding of the materials, and then to place a single mechanical connector, such as stitch line 180 or adhesive or thermal welding, to secure the first leg portion 144 to the second leg portion 154, where the single connector closes the leg section 140 and isolates the end 138 of the head section 130 outside of the closed space formed between the leg portions 144, 154.

In one embodiment, the first leg portion 144 is the same length as the second leg portion 154, such that the middle portion 142 is located equidistant between the first end 146 and the second end 156 of the leg section 140. In one embodiment, the first leg portion 144 has a different length than the second leg portion 154.

The support 120 is selected to be bio-compatible with implantation into a human body and is configured to allow tissue to grow through the head section 130 and the leg section 140 to anchor the support 120 in the body after implantation and healing. Suitable materials for the support 120 include autograft material (the patient's own tissue), allograft material (tissue from a cadaver), xenograft material (tissue from another species), or synthetic materials such as knitted meshes, woven fabrics or meshes, nonwoven fabrics or meshes, fibrillated fibers, or spun and fibrillated fibers. The support 120 is provided with voids including major spaces and smaller pores. The voids allow tissue ingrowth into and through the support 120. The major spaces have a size in a range from 1-10 mm and the pores have a size in a range from 50-200 µm.

In one embodiment, the support 120 is a knitted monofilament polypropylene mesh with the head section 130 provided with a heavier weight per area than the leg section 140.

One suitable head section 130 is knitted with a 100 µm monofilament polypropylene fiber into a knit structure having a thickness in a range from 0.3-0.5 mm and a weight per area in a range from 30-50 g/m$^2$, and preferably with a weight per area of approximately 34 g/m$^2$.

One suitable leg section 140 is knitted with an 80 µm monofilament polypropylene fiber into a knit structure having a thickness in a range from 0.25-0.36 mm and a weight per area in a range from 17-29 g/m$^2$, and preferably with a weight per area of approximately 22 g/m$^2$.

The leg section 140 material is thin and light weight (i.e., the weight per area or basis weight is less than approximately 30 g/m$^2$) to provide a thin and comfortable mesh that is agreeable with the delicate vaginal tissue that contacts the mesh and is less likely to be sensed through the tissue layers by the patient.

The embodiments of the support provide a structure that keeps the heavier material of the head section 130 separated away from the sensitive tissue of the vagina. This is achieved by locating the heavier weight material of the head section 130 away from where the light weight material of the leg section 140 is attached (or attachable) to the vagina. Specifically, the end 138 of the second end portion 136 of the head section 130 terminates at and is located between the first connector 170 and the second connector 180.

Suitable knitted monofilament polypropylene mesh is available from Coloplast Corp., Minneapolis, MN.

The first connector 170 secures the head section 130 to the first leg portion 144 but does not secure the head section 130 to the second leg portion 154. That is to say, the first connector 170 extends through the head section 130 and only the first leg portion 144 and does not extend through the second leg portion 154. The first connector 170 is coupled to the head section 130 and only the first leg portion 144 and is not coupled to the second leg portion 154. The second connector 180 is coupled between the first leg portion 144 and the second leg portion 154, and is not coupled to the head section 130.

The leg section 140 and the head section 130 combine to provide a Y-shaped support when viewed from a side edge of the sacrocolpopexy support 120.

In one embodiment, the head section 130 has an anterior side 190 opposite of a posterior side 192, and the connector 170 secures the leg section 140 to only one of the anterior side 190 or the posterior side 192 of the head section 130.

The first connector 170 is coupled to not more than two layers of material of the support 120 and second connector 180 is coupled to not more than two layers (e.g., only the leg portions 144, 154) of material of the support 120. For example, the first connector 170 is a suture that is stitched through not more than two layers of material of the support 120 and the second connector 180 is a suture that is stitched only the leg portions 144, 154 of the support 120 and not through the head section 130. One suitable connector material is polypropylene monofilament, for example, an 80 µm monofilament polypropylene fiber. In one embodiment, the first connector 170 is separate and distinct from the second connector 180. In one embodiment, each of the connectors 170, 180 is formed by an interlocking stitch that is stitched across the full width of the support 120. The interlocking stitch is placed in a transverse direction, preferably parallel with the second end 138 of the head section 130.

The first connector 170 attaches the leg section 140 to the second end portion 136 of the head section 130. In one embodiment, the second end 138 of the head section 130 is located equidistantly between the connectors 170, 180. In one embodiment, the end 130 of the head section 130 is located closer to the first connector 170 that it is to the second connector 180, which additionally serves to separate the end 138 away from the light weight material of the leg section 140 that is ultimately attached to the vaginal tissue.

In one embodiment, the connector 180 connects the first leg portion 144 to the second leg portion 154 to form a closed space located between the first leg portion 144 and the second leg portion 154, and an entirety of the head section 130 is located outside of the closed space located between the first leg portion 144 and the second leg portion 154.

Figure 12:
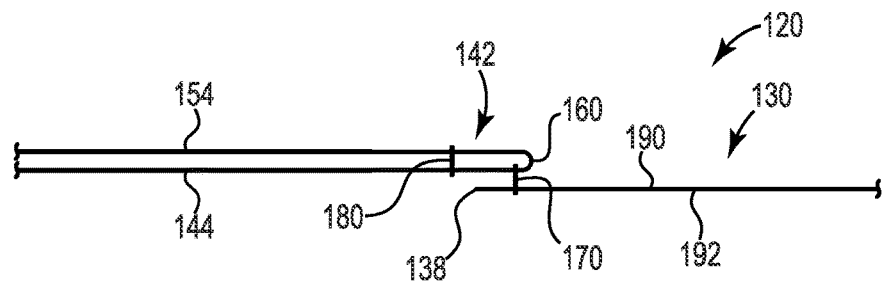
FIG. 12 is a side schematic view of the leg section connected to the head section of the sacrocolpopexy support.

FIG. 12 is a side schematic view of the first connector 170 and the second connector 180 locations.

The first connector 170 and the second connector 180 combine to provide what is termed a closed joint construction that separates the vaginal attachment portions of the lightweight structure of the leg section 140 away from the heavier structure of the head section 130. The closed joint construction is provided by aligning the open pores or open holes of the first leg portion 144 with the open holes of the head section 130 and then stitching a monofilament fiber through the open holes of the first leg portion 144 and the head section 130 to provide the first connector 170. The first connector 170 passes through only two layers, namely one leg portion 144 and the head section 130. A separate second stitch 180, spaced apart from the first connector 170, is passed through the aligned open holes of the first leg portion 144 and the second leg portion 154. The second connector passes through only the two layers of the leg portions 144, 154 and not through the head section 130.

In one embodiment, each stitch is formed in two passes, first in one direction across a width the support 120 and then in a reversed, second path across the width support 120. The advantage of a two-pass stitch pattern is realized in that twice-stitched closed joint resists separation when the support 120 is trimmed or cut. The two-pass stitch pattern forms a strong joint that allows the surgeon to cut the support 120 without the undesirable consequence of the leg section 140 separating from the head section 130.

In the illustrated embodiment, the head section 130 has an anterior side 190 opposite of a posterior side 192, and the first leg portion 144 and the second leg portion 154 are both located on only the anterior side 190 of the head section 130. This configuration contributes to the keeping the heavier structure of the head section 130 away from the sensitive tissue of the vagina that is supported by and attached to the lightweight structure of the leg section 140.

Figure 13:
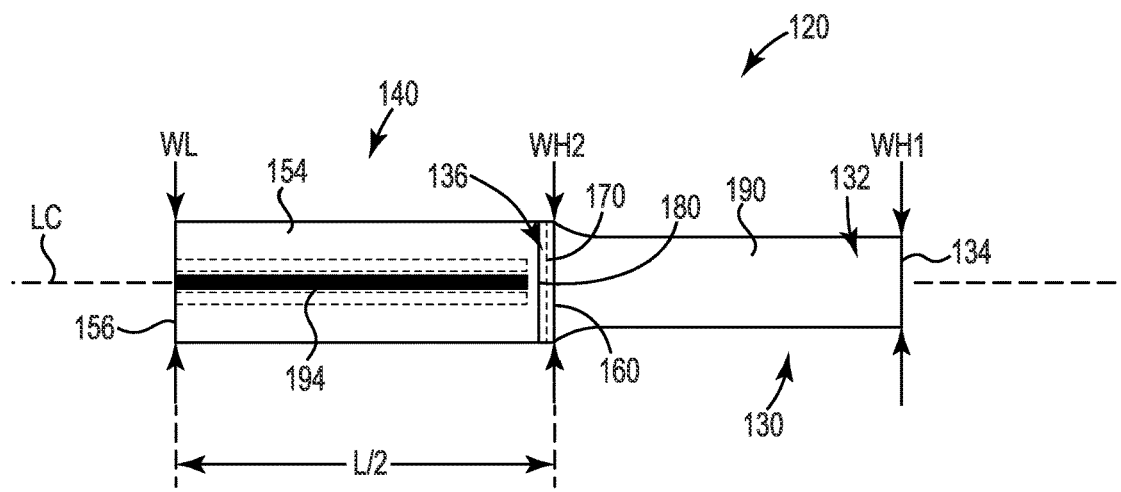
FIG. 13 is a front side view of the sacrocolpopexy support illustrated in FIG. 9.
Figure 14:
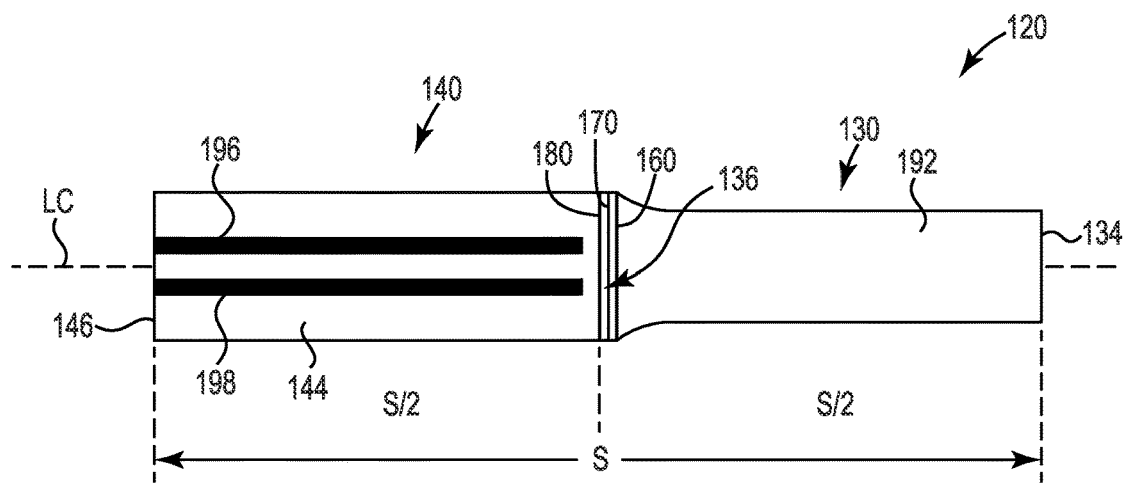
FIG. 14 is a back side view of the sacrocolpopexy support illustrated in FIG. 9.

FIG. 13 is a front view of the support 120 and FIG. 14 is a back view of the support 120. FIG. 13 is thus a top view of the second leg portion 154 and FIG. 14 is a view of the first leg portion 144.

The leg section 140 has a leg section length L and a leg section width WL (thus, the first leg portion 144 and the second leg portion 154 each have a length of L/2). The first connector 170 is connected to the second end portion 136 of the head section 130. A width WH2 of the second end portion 136 of the head section 130 is equal to the leg section width WL and is larger than a width WH1 of the first end portion 132 of the head section 130. In this manner, the head section 130 diverges from a narrower width WH1 at the first end 134 to a wider width WH2 at the second end section 136, and the width WH2 is equal to the width WL of the leg section 140. Thus, a transverse width of the leg section 140 (WL) is greater than a transverse width of the first end portion 132 of the head section 130 (WH1).

The support 120 is configured such that a distance S/2 measured from the second connector 180 to the first end 146 of the leg section 140 is equal to a distance S/2 measured from the second connector 180 to the end 134 of the head section 130. The total length of the support 120 is S (S/2 plus S/2).

In one embodiment, the support 120 has a single line 194 printed in ink on the second leg portion 154, with the single line 194 located longitudinally on a longitudinal center LC of the second leg portion 154.

In one embodiment, the support 120 has dual lines printed on the first leg portion 144. For example, a first line 196 is printed in ink on the first leg portion 144 and a second line 198 is printed in ink on the first leg portion 144, with each of the first line 196 and the second line 198 located longitudinally on the first leg portion 144 and offset away from the longitudinal center LC of the support 120 and the first leg portion 144.

The printed lines provide a guide to allow the surgeon to place the leg section 140 in a desired orientation. The printed lines are an optional feature for the support 120.

Figure 15:
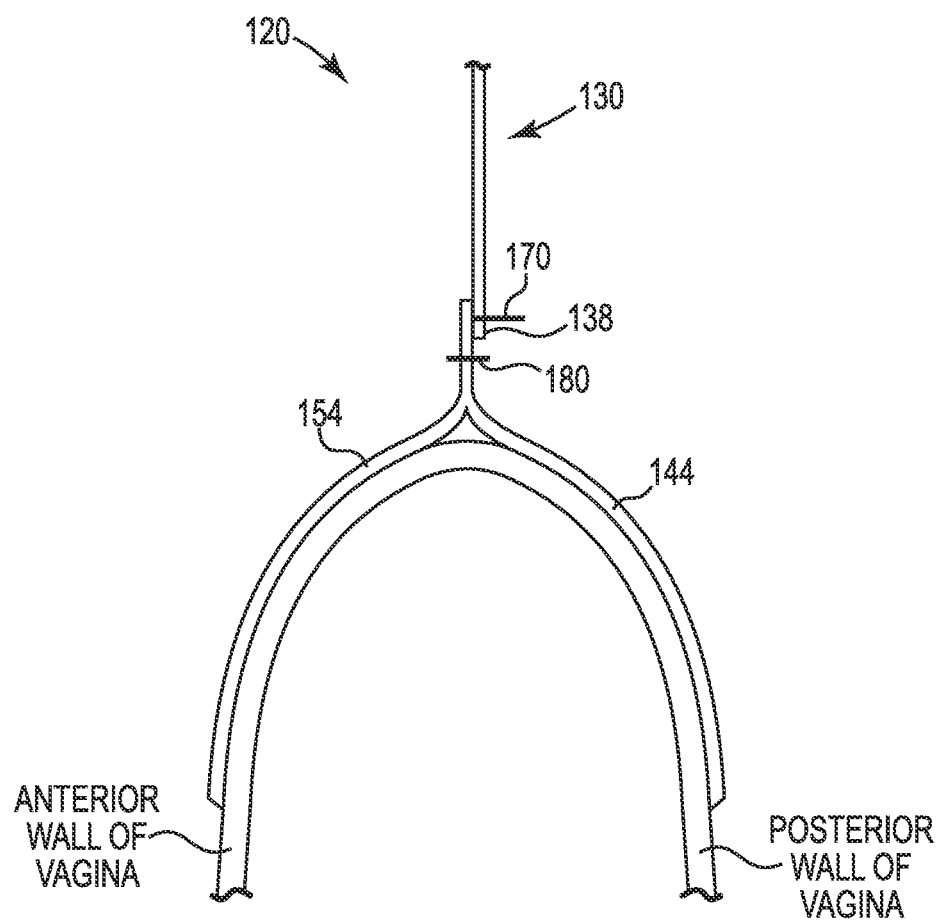
FIG. 15 is a schematic side view of the sacrocolpopexy support illustrated in FIG. 9 secured to a vagina of the patient.

FIG. 15 is a schematic side view of the sacrocolpopexy support 120 secured to a vagina of a patient. The head section 130 extends superior to the where it is attached to the sacrum and the leg section 140 extends inferior where it is attached to the cuff of the vagina. The first leg portion 144 has been secured to the posterior wall of the vagina and the second leg portion 154 has been secured to the anterior wall of the vagina. Suitable securement devices such as sutures or staples are employed for fixation, depending upon the preference of the surgeon. The lighter weight material of the leg portions 144, 154 are the only portion of the support 120 that is in contact with the delicate tissue of the vagina. The head section 130, fabricated from a heavier material than the leg section 140, is isolated and separated away from the delicate tissue of the vagina by locating the end 138 of the head section 130 between the second connector 180 and the first connector 170. The second connector 180 passes through and couples the leg portions 144, 154 together to form the closed joint, and this ensures that the heavier weight head section 130 is separated away from the attachment location of the leg section 140 to the vagina, and thus only the light weight and comfortable material of the leg section 140 is in contact with the sensitive tissue of the vagina.

Figure 16:
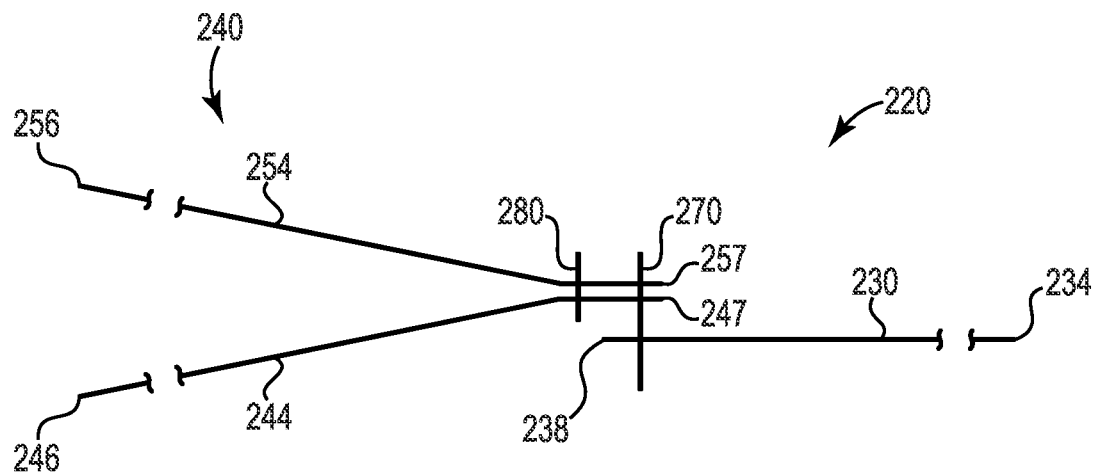
FIG. 16 is a schematic side view of one embodiment of a sacrocolpopexy support.

FIG. 16 is a schematic side view of one embodiment of a sacrocolpopexy support 220.

The support 220 has a head section 230 extending between a first end 234 and a second end 238 and a leg section 240. The leg section 240 has a first leg portion 244 extending between ends 246 and 247, and a second leg portion 254 extending between ends 256 and 257. The leg portions 244, 254 are aligned one on top of the other and secured by a first connector 270 and a second connector 280. The first connector 270 passes through and couples the leg portions 244, 254 to the head section 230. The second connector 280 passes through and couples the leg portions 244, 254. The second connector 280 is not coupled to the head section 230 and operates to close off the head section 230 and separate the head section 230 from the sensitive tissues of the vagina. In one embodiment, the second end 238 of the head section 230 is located between the first and second connectors 270, 280 to isolate and separate the head section 230 from the location where the leg section 240 is attached to the sensitive vaginal tissue.

In one embodiment, the second end 238 of the head section 230 is located on one side of the leg section 240, for example on the side of the first leg portion 244 opposite from the second leg portion 254, and the second connector 280 is placed to close off the possibility of the head section 230 from touching or abrading the sensitive vaginal tissue.

In one embodiment, the support 220 is a knitted monofilament polypropylene mesh with the head section 230 provided with a heavier weight per area than the leg section 240.

One suitable head section 230 is knitted with a 100 μm monofilament polypropylene fiber into a knit structure having a thickness in a range from 0.3-0.5 mm and a weight per area in a range from 30-50 g/m$^2$, and preferably with a weight per area of approximately 34 g/m$^2$.

One suitable leg section 140 is knitted with an 80 μm monofilament polypropylene fiber into a knit structure having a thickness in a range from 0.25-0.36 mm and a weight per area in a range from 17-29 g/m$^2$, and preferably with a weight per area of approximately 22 g/m$^2$.

The leg section 240 material is thin and light weight (i.e., the weight per area or basis weight is less than approximately 30 g/m$^2$) to provide a thin and comfortable mesh that is agreeable with the delicate vaginal tissue that contacts the mesh and is less likely to be sensed through the tissue layers by the patient.

The support 220 provides a structure that keeps the heavier material of the head section 230 separated away from the sensitive tissue of the vagina. This is achieved by locating the heavier weight material of the head section 230 away from where the light weight material of the leg section 240 is attached (or attachable) to the vagina. Specifically, the end 238 of the head section 230 terminates at and is located between the first connector 270 and the second connector 280, which ensures that the heavier head section is not able to contact the walls or tissue of the vagina.

It is acceptable to secure the leg section 240 to the head section 230 by, for example, securing first leg portion 244 to the head section 230 with adhesive or by thermal welding of the materials, and then to place a single mechanical connector, such as stitch line 280 or adhesive or thermal welding, to secure the first leg portion 244 to the second leg portion 254, where the single connector closes the leg section 240 and isolates the end 238 of the head section 230 outside of the closed space formed between the leg portions 244, 254.

Figure 17:
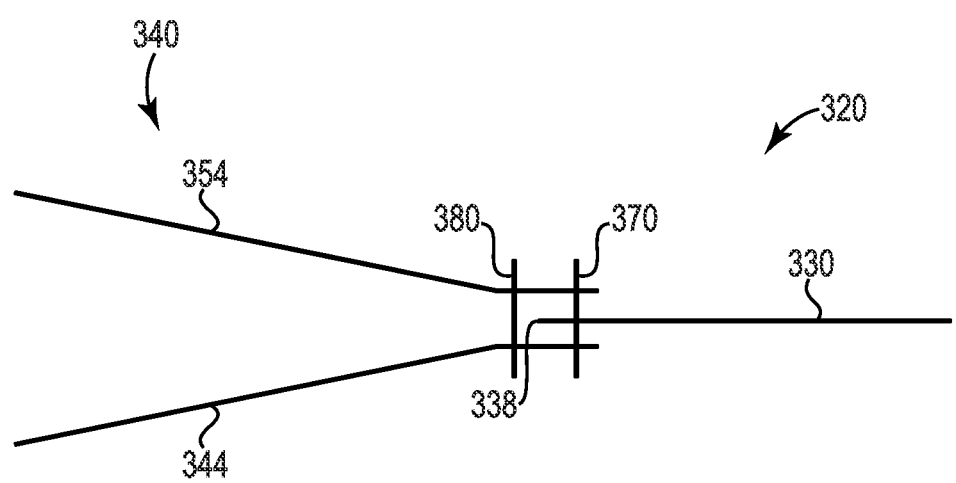
FIG. 17 is a schematic side view of one embodiment of a sacrocolpopexy support.

FIG. 17 is a schematic side view of one embodiment of a sacrocolpopexy support 320.

The support 320 has a head section 330 terminating at an end 338 and a leg section 340. The leg section 340 has a first leg portion 344 and a second leg portion 354. The leg portions 344, 354 are aligned one on top of the other and secured by a first connector 370 and a second connector 380. The first connector 370 passes through and couples the leg portions 344, 354 to the head section 330. The second connector 380 closes the leg portions 344, 354 and isolates the end 338 of the head section 330 outside of the V-shape formed by the leg portions 344, 354. The second connector 380 is not coupled to the head section 330 and operates to separate the head section 330 away from the area where the V-shape of the leg section 340 engages with the sensitive tissues of the vagina. In one embodiment, the end 338 of the head section 330 is located between the first and second connectors 370, 380 to isolate and separate the head section 330 from the location where the leg section 340 is attached to the sensitive vaginal tissue.

In one embodiment, the second end 338 of the head section 330 is located, or sandwiched, between the first and second leg portions 344, 354 and the second connector 380 is placed to close the head section 330 from entering the V-shape of the leg section 340 that engages with the sensitive tissues of the vagina.

It is acceptable to secure the leg section 340 to the head section 330 by, for example, securing first leg portion 344 to the head section 330 with adhesive or by thermal welding of the materials, and then to place a single mechanical connector, such as stitch line 380 or adhesive or thermal welding, to secure the first leg portion 344 to the second leg portion 354, where the single connector closes the leg section 340 and isolates the end 338 of the head section 330 outside of the closed space formed between the leg portions 344, 354.

Embodiments include the following examples.

Example 1 is a sacrocolpopexy support comprising:
a head section extending from a first end portion to a second end portion;
a leg section having a middle portion, a first leg portion extending from the middle portion to a first end of the leg section, and a second leg portion extending from the middle portion to a second end of the leg section;
a fold formed in the leg section such that the first leg portion is folded into contact with the second leg portion;
a first connector securing the head section to the first leg portion and not securing the head section to the second leg portion; and
a second connector securing the head section to the first leg portion and securing the head section to the second leg section.

Example 2 adds to Example 1, where the head section has an anterior side opposite of a posterior side, and the first leg portion and the second leg portion are both located on only the anterior side of the head section.

Example 3 adds to Example 1, where the leg section is a single integrated piece of material with the middle portion located equidistant between the first end of the leg section and the second end of the leg section.

Example 4 adds to Example 1, the leg section has a leg section width, and the first connector and the second connector are connected to the second end portion of the head section; and a width of the second end portion of the head section is equal to the leg section width and is larger than a width of the first end portion of the head section.

Example 5 adds to Example 1, where the first connector is closer to the fold than the second connector is to the fold.

Example 6 adds to Example 1, where the first connector is a suture that is stitched through not more than two layers of material of the sacrocolpopexy support.

Example 7 adds to Example 1, where the second connector is a suture that is stitched through three layers of material of the sacrocolpopexy support.

Example 8 adds to Example 1, a length of the first leg portion measured from the fold to the first end of the leg section is equal to a length of the second leg portion measured from the fold to the second end of the leg section.

Example 9 adds to Example 1, where a distance measured from the second connector to the first end of the leg section is equal to a distance measured from the second connector to an end of the first end portion of the head section.

Example 10 adds to Example 1, where a transverse width of the leg section is greater than a transverse width of the first end portion of the head section.

Example 11 adds to Example 1, where a basis weight of the leg section is less than 30 g/m$^2$.

Example 12 adds to Example 1, where a basis weight of the first leg portion is equal to a basis weight of the second leg portion.

Example 13 adds to Example 1, where a basis weight of the leg section is less than 30 g/m$^2$ and a basis weight of the head section is greater than 30 g/m$^2$.

Example 14 adds to Example 1, where a single line is printed in ink on the second leg portion and located longitudinally on a longitudinal center of the second leg portion.

Example 15 adds to Example 1, where a first line is printed in ink on the first leg portion and a second line printed in ink on the first leg portion, with each of the first line and the second line located longitudinally on the first leg portion and offset away from a longitudinal center of the first leg portion.

Although specific embodiments have been illustrated and described in this disclosure, it will be appreciated by those of ordinary skill in the art that a variety of alternate and/or equivalent implementations may be substituted for the specific embodiments shown and described without departing from the scope of this disclosure. This application is intended to cover any adaptations or variations of the above-disclosed medical devices. Therefore, it is intended that this invention is limited only by the claims and their equivalents.

The invention claimed is:

1. A sacrocolpopexy support comprising:
a Y-shaped support comprising a head section having a first free end and a second end secured to a leg section, with the leg section comprising a first leg extending from the second end of the head section and a second leg extending from the second end of the head section;
wherein the head section is a knit structure having a head fiber knitted to define open head spaces in the head section;
wherein the leg section is a knit structure having a leg fiber knitted to define open leg spaces in the leg section, with the first leg placed over the second leg to align the open leg spaces of the leg section;
a first connector provided as a first interlocking stitch, with the first interlocking stitch passed through the open leg spaces of the first leg and the open head spaces in the head section; and
a second connector provided as a second interlocking stitch, with the second interlocking stitch passed through the aligned open leg spaces of the first leg and the second leg to connect the first leg to the second leg;
wherein the second end of the head section is located outside a space where the first leg is connected to the second leg.

2. The sacrocolpopexy support of claim 1, wherein the head fiber and the leg fiber are provided by a single fiber that is knitted into the knit structure of the head section and the knit structure of the leg section.

3. The sacrocolpopexy support of claim 1, wherein the first interlocking stitch is stitched across a full width of the head section.

4. The sacrocolpopexy support of claim 1, wherein the first interlocking stitch is not passed through the second leg, and the second interlocking stitch is passed through the aligned open leg spaces of the first leg and the second leg and the open head spaces in the head section to connect the first leg to the second leg and to the head section.

5. The sacrocolpopexy support of claim 1, wherein the first interlocking stitch is not passed through the second leg, and the second interlocking stitch is passed through the aligned open leg spaces of the first leg and the second leg and not through the head section.

6. The sacrocolpopexy support of claim 1, wherein the knit structure of the head section is knitted from a monofilament polypropylene fiber into a weight per area in a range from 30-50 g/m².

7. The sacrocolpopexy support of claim 1, wherein the knit structure of the leg section is knitted from a monofilament polypropylene fiber into a weight per area in a range from 17-29 g/m².

8. The sacrocolpopexy support of claim 1, wherein the first free end of the head section is narrower than the leg section.

9. The sacrocolpopexy support of claim 1, wherein the head section has a weight per area that is greater than a weight per area of the first leg and a weight per area of the second leg, and the head section is separated and isolated away from a location between the first leg and the second leg.

10. A sacrocolpopexy support comprising:
a Y-shaped support comprising a head section having a first free end and a second end secured to a leg section, with the leg section comprising a first leg extending from the second end of the head section and a second leg extending from the second end of the head section;
wherein the head section is a knit structure having a head fiber knitted to define open head spaces in the head section;
wherein the leg section is a knit structure having a leg fiber knitted to define open leg spaces in the leg section, with the first leg placed over the second leg to align the open leg spaces of the leg section;
a first connector provided as a first interlocking stitch, with the first interlocking stitch passed through the open leg spaces of the first leg and the open head spaces in the head section, and the first interlocking stitch is not passed through the second leg; and
a second connector provided as a second interlocking stitch, with the second interlocking stitch passed through the aligned open leg spaces of the first leg and the second leg to connect the first leg to the second leg;
wherein the head section has a weight per area that is greater than a weight per area of the first leg and a weight per area of the second leg, and the head section is located outside a space where the first leg is connected to the second leg.

11. The sacrocolpopexy support of claim 10, wherein the second interlocking stitch is passed through the aligned open leg spaces of the first leg and the second leg and the open head spaces in the head section to connect the first leg to the second leg and to the head section.

12. The sacrocolpopexy support of claim 10, wherein the head fiber and the leg fiber are provided by a single fiber that is knitted into the knit structure of the head section and the knit structure of the leg section.

* * * * *